United States Patent [19]

Kampe et al.

[11] 4,370,323
[45] Jan. 25, 1983

[54] 2-CYANOAZIRIDINYL-(1)-2-SUBSTITUTED-AZIRIDINYL-(1)-METHANES

[75] Inventors: Wolfgang Kampe, Heddesheim; Max Thiel, Mannheim; Erich Fauland, Mannheim-Gartenstadt; Uwe Bicker, Mannheim; Gottfried Hebold, Mannheim-Vogelstang, all of Fed. Rep. of Germany

[73] Assignee: Boehringer Mannheim GmbH, Mannheim, Fed. Rep. of Germany

[21] Appl. No.: 776,068

[22] Filed: Mar. 9, 1977

[30] Foreign Application Priority Data

Mar. 11, 1976 [DE] Fed. Rep. of Germany ....... 2610156

[51] Int. Cl.³ ............... C07D 403/06; C07D 403/14; C07D 401/14; A61K 31/395
[52] U.S. Cl. ............................... 424/244; 260/239 E; 260/330.3; 546/112; 546/208; 546/275; 548/518; 424/263; 424/267; 424/274; 424/275; 424/276; 424/278; 260/330.9
[58] Field of Search .................... 260/239 E; 424/244

[56] References Cited

U.S. PATENT DOCUMENTS 3,828,024  8/1974  Breslow ......................... 260/239 E

OTHER PUBLICATIONS

Bicker et al., Exp. Pathology Bd. 15, S 49–62, (1978).
Bicker, Fort. Med. 96 Jg, (1978), Nr 12, pp. 661–664.
Bicker et al, IRCS Med. Sci. Cancer, Hamatology, Immunology & Allergy; Microbiology; Paracitology, Pharm 5, 299, 399 523; 6, 215, 455.
Szeimies, Chem. Ber 106, 3695–3697, (1973).
Gundermann et al, Chem. Ber 105, 312–314, (1972).

Primary Examiner—Mark L. Berch

Attorney, Agent, or Firm—Sprung, Horn, Kramer & Woods

[57] ABSTRACT

A 2-cyanoaziridinyl-(1)-2-substituted-aziridinyl-(1)-methane

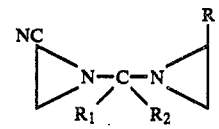

wherein
R is a nitrile or carbamoyl group, and
$R_1$ and $R_2$ each independently is a hydrogen atom, an aliphatic hydrocarbon radical containing up to 10 carbon atoms optionally substituted by hydroxyl, alkoxy, amino, alkylamino, dialkylamino, alkoxycarbonyl, cyano, 1, 2 or 3 halogens, cycloalkyl, phenyl or phenoxy; nitrile, carboxyl, alkoxycarbonyl or optionally hydrogenated monocyclic heteroaryl or phenyl optionally substituted by alkyl, alkoxy, hydroxy, alkoxcarbonyl, dialkylamino, alkylthio, trifluoromethyl, nitro, carbamoyl, nitrile, sulphonamido, hydroxyalkyl, methylenedioxy, or halogen; or $R_1$ and $R_2$, together with the carbon atom to which they are attached, form a ring containing up to 8 ring members of which at least one may be oxygen, sulphur, SO, $SO_2$, NH, N-alkyl, N-acyl or N-alkoxycarbonylalkyl, and which can be substituted by alkyl, alkoxy, hydroxyl, alkylenedioxy, alkoxycarbonyl, hydroxyalkyl, alkoxycarbonylalkyl, dialkylamino, oxo or 2-cyanoaziridino groups, or can be fused to 1 or 2 benzene rings or can be bridged by alkylene radicals containing up to 3 carbon atoms.

The compounds are characterized by cytostatic and immune response-stimulating activity.

12 Claims, No Drawings

2-CYANOAZIRIDINYL-(1)-2-SUBSTITUTED-AZIRIDINYL-(1)-METHANES

The present invention is concerned with new aziridine derivatives and with the preparation thereof.

Compounds with aziridine structures are biologically-active compounds which not only have mutagenic properties but also exhibit a cytostatic effectiveness. In German Democratic Republic Patent Specification No. 110,492, it is stated that 2-cyanoaziridine derivatives in which the aziridine nitrogen atom is acylated have a low toxicity and show a varying degree of cytostatic effectiveness in animal experiments.

According to German Patent Specification No. P 25 28 460.0, when 1-carboxamido-2-cyanoaziridine is administered intravenously, it displays not only a cytostatic action but also an immune-stimulating action, which is due to a marked increase of the number of leukocytes and lymphocytes, with substantially unchanged number of erythrocytes, as well as to an increase of the antibody-forming spleen cells.

Since most other cytostatics are immune-suppressive and thus increase the susceptibility of the patients, who are in any case weakened by cancer diseases, to other diseases, 1-carboxyamino-2-cyanoaziridine is, in principle, very valuable. However, a disadvantage of this compound is that, because of its acid lability, it can practically only be administered intravenously and, even in a buffered aqueous solution, can only be kept for a short time.

Consequently, there is a need to find other derivatives of 2-cyanoaziridine which, with an equal or increased cytostatic and/or immune-stimulating action, are stable and can possibly also be administered orally.

According to the present invention, there are provided new aziridine derivatives of the general formula:

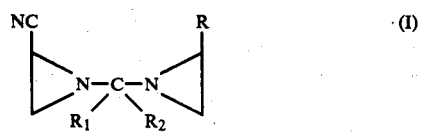

wherein R is a nitrile or carbamoyl group and $R_1$ and $R_2$, which can be the same or different, are hydrogen atoms or aliphatic hydrocarbon radicals containing up to 10 and preferably up to 6 carbon atoms, which can be straight-chained, branched, cyclic, saturated or unsaturated and optionally substituted by hydroxyl, alkoxy, amino, alkylamino, dialkylamino, alkoxycarbonyl, cyano, 1, 2 or 3 halogens, cycloalkyl, phenyl or phenoxy, or are nitrile, carboxyl, alkoxycarbonyl or optionally hydrogenated monocyclic heteroaryl or phenyl radicals which are optionally substituted by alkyl, alkoxy, hydroxy, alkoxycarbonyl, dialkylamino, alkylthio, trifluoromethyl, nitro, carbamoyl, nitrile, sulphonamide, hydroxyalkyl or methylenedioxy groups or by halogen, or $R_1$ and $R_2$, together with the carbon atom to which they are attached, can also form a saturated or unsaturated ring containing up to 8 ring members, which ring can also be interrupted by oxygen, sulphur, SO, $SO_2$, NH, N-alkyl, N-acyl or N-alkoxycarbonylalkyl and/or can be substituted by alkyl, alkoxy, hydroxyl, alkylenedioxy, alkoxycarbonyl, hydroxyalkyl, alkoxycarbonylalkyl, dialkylamino, oxo or 2-cyanoaziridino groups, or can be fused to 1 or 2 benzene rings or bridged by alkylene radicals containing up to 3 carbon atoms.

Alkyl, alkoxy and alkylene radicals are to be understood, if not stated to the contrary, to be radicals containing up to 6 and preferably up to 3 carbon atoms, methyl and ethyl radicals being especially preferred in the case of alkyl radicals.

Cycloalkyl radicals are to be understood to be radicals containing 3 to 10 carbon atoms, cyclopropyl, cyclopentyl and cyclohexyl radicals being preferred.

Unsaturated monocyclic heteroaryl radicals are to be understood to be, in particular, thiophene, furan, pyrrole, N-alkylpyrrole, pyridine, pyridine-N-oxide, imidazole, pyrazole, pyrimidine, isoxazole and pyrazine rings. Hydrogenated or unsaturated heteroaryl radicals are to be understood to be especially dihydropyran, tetrahydropyran, pyrrolidine, imidazolidine, imidazoline, pyridazoline, piperidine, piperazine, morpholine, tetrahydrofuran and tetrahydrothiophene rings.

Carbocycles which can be formed from $R_1$ and $R_2$ are preferably cyclopentane, cyclohexane, cycloheptane and cyclooctane. An unsaturated ring, cyclohexene is preferred. Ring systems fused with benzene rings are preferably fluorene, indane and tetrahydronaphthalene and ring systems bridged with alkylene are preferably adamantane and bicyclo[2.2.1]heptane.

Heterocycles which are formed from $R_1$, $R_2$ and the carbon atom to which they are attached are preferably tetrahydropyran, tetrahydrothiopyran and piperidine; heterocycles annelated with benzene rings are preferably dibenzoxepin, xanthene and chromane. A ring system bridged with alkylene is preferably N-methyl-9-azabicyclo[3.3.1]nonane.

By halogen atoms, there are to be understood fluorine, chlorine and bromine atoms, fluorine and chlorine atoms being preferred.

Acyl is preferably an alkylcarbonyl radical but can also be any other conventional acid residue, for example of an aromatic or araliphatic carboxylic acid, especially benzoic acid, or of a pharmacologically compatible sulphonic acid.

The present invention also includes within its scope all stereoisomeric forms of the compounds of general formula (I) which occur due to the presence of the asymmetrical carbon atoms as well as nitrogen atoms.

The compounds of general formula (I) exhibit very strong immune-stimulating and cancerostatic properties, lead to a stimulation of the bone marrow and of the reticulo-endothelial system with increased formation of cells of the erythropoietic series and the release of these cells into the peripheral blood system and, in addition, strengthen resistance against bacterial infection. In addition, the compounds (I) are able to bring about immune restoration.

The new compounds (I) according to the present invention can be prepared, for example, by reacting a carbonyl compound of the general formula:

wherein $R_1$ and $R_2$ have the same meanings as above, or a reactive derivative thereof, with 2-cyanoaziridine and 2-carbamoylaziridine in a mole ratio of about 10:3-100-:0-10 and subsequently, if desired, converting a carbamoyl group into a nitrile group by means of a hydration agent.

The process according to the present invention can be carried out in an organic solvent which is inert under the reaction conditions, for example, ethyl acetate, diethyl ether, toluene, dioxan, ethylene glycol dimethyl ether or acetonitrile, but, in many cases, the addition of solvents can be omitted since the carbonyl compound used can also serve as a solvent.

The reaction of the process according to the present invention can be accelerated by the addition of an organic or inorganic base, for example trimethylamine, triethylamine, tributylamine, diisopropylethylamine, diazabicyclooctane, anhydrous potassium carbonate, magnesium carbonate, magnesium oxide or basic aluminum oxide. It is also possible to add small amounts of an acidic catalyst which normally accelerates aminal formation, for example an inorganic or organic acid, acid chloride, a phenol or an ammonium salt.

The process is usually carried out at a temperature of about 0° to 100° C. and preferably of about 20° to 60° C.

As is to be expected, the rate of reaction is the lower, the lower is the reaction temperature but, on the other hand, at a low temperature, less by-products and decomposition products are formed.

From stoichiometric considerations, for the process according to the present invention, the required mole ratio of carbonyl compound to aziridine is 10:20, in the case of which the most favorable yields are also obtained. On the other hand, when the mole ratio is varied, the yield is not so substantially changed that an excess of one or other of the reaction components becomes pointless. When using expensive carbonyl compounds or when it is desired to obtain compounds in which R is a nitrile, 2-cyanoaziridine is, therefore, used in excess. When using inexpensive carbonyl compounds, these can simultaneously be used as solvent. In other words, they can be used in excess.

2-Carbamoylaziridine is to be employed especially when using a derivative of the carbonyl compound or in the presence of a water-binding agent. In general, a mole ratio of carbonyl compound to 2-cyanoaziridine to 2-carbamoylaziridine of about 10:3–20:0–10 is favorable and mole ratios of about 10:15–20:0 in the case of normal carbonyl compounds or of about 10:10–15:10 in the case of reactive carbonyl compounds are preferred. In order to obtain compounds in which R is a nitrile group, mole ratios of carbonyl compound to 2-cyanoaziridines of about 10:30–100 are favorable, a ratio of about 10:50–100 being preferred and also, instead of the carbonyl compound, there can be used compounds of general formula (I) in which R is carbamoyl which are obtained as intermediate products.

Reactive derivatives of carbonyl compounds of general formula (II) are to be understood to be, for example, ketals, acetals, dihalo compounds and the like. The reaction of these reactive derivatives of general formula (II) with 2-cyanoaziridines can be catalyzed by the addition of acid-binding agents.

As acid-binding agents, there can be used organic and inorganic bases, for example, diisopropylethylamine, solid potassium hydroxide, barium hydroxide, potassium carbonate, magnesium oxide or silver carbonate.

As reagents for the dehydration of the carbamoyl group, there can be used, for example, methanesulphochloride, benzene-sulphochloride, toluene-sulphochloride, ethyl chloroformate, N,N'-bicyclohexylcarbodiimide, phosphorus oxychloride, phosphorus pentachloride or triphenyl phosphine/carbon tetrachloride.

2-Cyanoaziridine can be prepared, for example, from $\alpha,\beta$-dibromopropionitrile and ammonia in the manner described by K. Burzin et al. (Ang. Chem., 84, 108/1972).

The preparation of 2-carbamoylaziridine has been described by E. Kyburz et al. (Helv. Chim. Acta, 49, 359/1966).

For the preparation of pharmaceutical compositions with immune-stimulating and cancerostatic action, the compounds of general formula (I) are mixed in the usual manner with solid or liquid pharmaceutical diluents or carriers. These pharmaceutical compositions can be, for example, in the form of tablets or dragees. The compounds (I) can, with the addition of appropriate adjuvants, be suspended or dissolved in water or an oil, for example olive oil, and placed into capsules. Since the active material is acid-labile, the composition is provided with a coating which is first soluble in the alkaline medium of the intestines or it is mixed with an appropriate carrier material, for example a high molecular weight fatty acid or carboxymethylcellulose. Solid carrier materials include, for example, starch, lactose, mannitol, methyl cellulose, talc, highly-dispersed silicic acid, high molecular weight fatty acids (such as stearic acid), gelatin, agar-agar, calcium phosphate, magnesium stearate, animal and vegetable fats and solid high molecular weight polymers (such as polyethylene glycol). Compositions which are suitable for oral administration can, if desired, contain flavoring and sweetening materials.

As injection medium, it is preferable to use water which contains the conventional additives for injection solutions, such as stabilizing agents, solubilizing agents or weakly alkaline buffers. Additives of this kind include, for example, phosphate and carbonate buffers, ethanol, complex-forming agents (such as ethylenediaminetetraacetic acid and the non-toxic salts thereof) and high molecular weight polymers (such as polyethylene oxide) for viscosity regulation.

Apart from the compounds mentioned in the following examples, the following compounds are also preferred according to the present invention:

(1) 2-[2-cyanoaziridinyl-(1)]-2-[2-carbamoylaziridinyl-(1)]-1-hydroxypropane;

(2) 1-[2-cyanoziridinyl-(1)]-1-[2-carbamoylaziridinyl-(1)]-1-cyanoethane;

(3) 4-[2-cyanoaziridinyl-(1)]-4-[2-carbamoylaziridinyl-(1)]-2,6-dimethyl-n-heptane;

(4) 1-[2-cyanoaziridinyl-(1)]-1-[2-carbamoylaziridinyl-(1)]-1-cyclopentyl-3-methyl-butane;

(5) 1-[2-cyanoaziridinyl-(1)]-1-[2-carbamoylaziridinyl-(1)]-cyclohexyl-n-butane;

(6) [2-cyanoaziridinyl-(1)]-[2-carbamoylaziridinyl-(1)]-dicyclopropyl-methane;

(7) [2-cyanoaziridinyl-(1)]-[2-carbamoylaziridinyl-(1)]-dicyclopentyl-methane;

(8) [2-cyanoaziridinyl-(1)]-[2-carbamoylaziridinyl-(1)]-cyclopentyl-cyclohexyl-methane;

(9) 1-[2-cyanoaziridinyl-(1)]-1-[2-carbamoylaziridinyl-(1)]-1-cyclopentyl-2-cyclohexyl-ethane;

(10) 1-[2-cyanoaziridinyl-(1)]-1-[2-carbamoylaziridinyl-(1)]-2-ethoxycarbonyl-cyclohexane; m.p. 123°–126° C.

(11) 1-[2-cyanoaziridinyl-(1)]-1-[2-carbamoylaziridinyl-(1)]-indane;

(12) 1-[2-cyanoaziridinyl-(1)]-1-[2-carbamoylaziridinyl-(1)]-2-cyclohexane;

(13) 1-[2-cyanoaziridinyl-(1)]-1-[2-carbamoylaziridinyl-(1)]-1-p-hydroxyphenyl-ethane;
(14) [2-cyanoaziridinyl-(1)]-[2-carbamoylaziridinyl-(1)]-cyclohexylphenyl-methane;
(15) [2-cyanoaziridinyl-(1)]-[2-carbamoylaziridinyl-(1)]-di-[thienyl-(2)]-methane;
(16) 4-[2-cyanoaziridinyl-(1)]-4-[2-carbamoylaziridinyl-(1)]-tetrahydrothiapyran;
(17) 4-[2-cyanoaziridinyl-(1)]-4-[2-carbamoylaziridinyl-(1)]-1-methylpiperidine;
(18) 4-[2-cyanoaziridinyl-(1)]-4-[2-carbamoylaziridinyl-(1)]-1-ethoxycarbonylmethyl-piperidine;
(19) 4-[2-cyanoaziridinyl-(1)]-4-[2-carbamoylaziridinyl-(1)]-1-acetylpiperidine;
(20) 3-[2-cyanoaziridinyl-(1)]-3-[2-carbamoylaziridinyl-(1)]-tetrahydropyran;
(21) 1-[2-cyanoaziridinyl-(1)]-1-[2-carbamoylaziridinyl-(1)]-1-[furyl-(2)]-ethane;
(22) 1-[2-cyanoaziridinyl-(1)]-1-[2-carbamoylaziridinyl-(1)]-1-[thienyl-(2)]-ethane;
(23) 11-[2-cyanoaziridinyl-(1)]-11-[2-carbamoylaziridinyl-(1)]-6-H-dibenz[b,c]oxepin;
(24) 1-[2-cyanoaziridinyl-(1)]-1-[2-carbamoylaziridinyl-(1)]-2,2,2-trichloroethane;
(25) ethyl [2-cyanoaziridinyl-(1)]-[2-carbamoylaziridinyl-(1)]-acetate;
(26) 1-[2-cyanoaziridinyl-(1)]-1-[2-carbamoylaziridinyl-(1)]-2-phenyl-ethane;
(27) [2-cyanoaziridinyl-(1)]-[2-carbamoylaziridinyl-(1)]-(4-hydroxymethylphenyl)-methane;
(28) 1-[2-cyanoaziridinyl-(1)]-1-[2-carbamoylaziridinyl-(1)]-prop-2-ene;
(29) 2-{[2-cyanoaziridinyl-(1)]-[2-carbamoylaziridinyl-(1)]-methyl}-pyrrole;
(30) 3-{[2-cyanoaziridinyl-(1)]-[2-carbamoylaziridinyl-(1)]-methyl}-pyridine;
(31) 4-{[2-cyanoaziridinyl-(1)]-[2-carbamoylaziridinyl-(1)]-methyl}-pyridine-1-oxide;
(32) 1-[2-cyanoaziridinyl-(1)]-1-[2-carbamoylaziridinyl-(1)]-1-phenyl-2-cyanoethane;
(33) 1,1-bis-[2-cyanoaziridinyl-(1)]-ethane m.p. 143°–145° C.;
(34) 2,2-bis-[2-cyanoaziridinyl-(1)]-propane m.p. 84°–86° C.;
(35) α,α-bis-[2-cyanoaziridinyl-(1)]-toluene m.p. 118°–121° C.; and
(36) 1,1-bis-[2-cyanoaziridinyl-(1)]-cyclohexane.

The following Examples are given for the purpose of illustrating the present invention:

EXAMPLE 1

2-[2-Cyanoaziridinyl-(1)]-2-[2-carbamoylaziridinyl-(1)]-propane

A mixture of 68.0 g. 2-cyanoaziridine, 116 g. acetone and 36.5 g. triethylamine is maintained at ambient temperature for 10 to 12 days. The crystals formed are filtered off with suction, washed with a little ethyl acetate/diethyl ether (1:1) and then recrystallized from ethyl acetate or acetone with the addition of active charcoal. There are obtained 28.0 g. (about 29% of theory) 2-[2-cyanoaziridinyl-(1)]-2-[2-carbamoylaziridinyl-(1)]-propane; m.p. 156°–158° C.

EXAMPLE 2

2-[2-Cyanoaziridinyl-(1)]-2-[2-carbamoylaziridinyl-(1)]-propane

A mixture of 34.0 g. 2-cyanoaziridine, 58.0 g. acetone and 18.0 g. triethylamine is warmed to 40° C. for 100 to 120 hours. After working up the reaction mixture in a manner analogous to that described in Example 1, there are obtained 14.0 g. (about 29% of theory) 2-[2-cyanoaziridinyl-(1)]-2-[2-carbamoylaziridinyl-(1)]-propane; m.p. 156°–158° C.

EXAMPLE 3

2-[2-Cyanoaziridinyl-(1)]-2-[2-carbamoylaziridinyl-(1)]-propane

The mother liquor of the crude crystallizate obtained according to Example 1 or 2 is evaporated in a vacuum. 25 g. of the honey-yellow or brown residue thus obtained are chromatographed on aluminum oxide (basic aluminum oxide; activity stage III) with ethyl acetate. The pure fractions are evaporated in a vacuum and the partially crystallized residue is triturated with diethyl ether and filtered off with suction, 10.3 g. of material being obtained. After recrystallization from about 20–25 ml. ethyl acetate, there are obtained 8.2 g. 2-[2-cyanoaziridinyl-(1)]-2-[2-carbamoylaziridinyl-(1)]-propane; m.p. 96°–98° C. Since the compound has the same overall composition and structural formula as the compound obtained according to Example 1 or 2, it must be a stereoisomeric form thereof.

EXAMPLE 4

2-[2-Cyanoaziridinyl-(1)]-2-[2-carbamoylaziridinyl-(1)]propane

A solution of 3.4 g. 2-cyanoaziridine, 4.3 g. 2-carbamoylaziridine and 11.6 g. acetone is warmed to 40° C. for 100–120 hours. The reaction mixture is thereafter evaporated in a vacuum and the brown residue obtained is recrystallized from ethyl acetate with the addition of active charcoal. There is obtained 1.36 g (about 14% of theory) 2-[2-cyanoaziridinyl-(1)]-2-[2-carbamoylaziridinyl-(1)]-propane; m.p. 154°–157° C.

EXAMPLE 5

2-[2-Cyanoaziridinyl-(1)]-2-[2-carbamoylaziridinyl-(1)]-1-fluoropropane

A mixture of 6.8 g. 2-cyanoaziridine and 7.6 g. monofluoroacetone is mixed, while cooling to 10°–12° C., with 0.6 ml. triethylamine. After standing for two days at ambient temperature, the reaction mixture is chromatographed on basic aluminum oxide (activity stage III; elution agent successively: heptane, diethyl ether, ethyl acetate). The fractions containing the desired product are evaporated to give an initially oily residue which, upon trituration with diethyl ether/ethyl acetate, crystallizes. There is obtained 0.9 g. 2-[2-cyanoaziridinyl-(1)]-2-[2-carbamoylaziridinyl-(1)]-1-fluoropropane; m.p. 136°–137° C.

In an analogous manner, there are obtained from
(a) 2-cyanoaziridine and chloroacetone in the presence of triethylamine:
2-[2-cyanoaziridinyl-(1)]-2-[2-carbamoylaziridinyl-(1)]-1-chloropropane; m.p. 145° C. (decomp.);
(b) 2-cyanoaziridine and trifluoroacetone in the presence of triethylamine:
2-[2-cyanoaziridinyl-(1)]-2-[2-carbamoylaziridinyl-(1)]-1,1,1-trifluoropropane;
(c) 2-cyanoaziridine and 1-methoxyacetone in the presence of triethylamine:
2-[2-cyanoaziridinyl-(1)]-2-[2-carbamoylaziridinyl-(1)]-1-methoxypropane; colorless syrup;

(d) 2-cyanoaziridine and 1-dimethylaminoacetone in the presence of triethylamine:
2-[2-cyanoaziridinyl-(1)]-2-[2-carbamoylaziridinyl-(1)]-1-dimethylaminopropane;

(e) 2-cyanoaziridine and 1,3-dihydroxyacetone in the presence of triethylamine:
2-[2-cyanoaziridinyl-(1)]-2-[2-carbamoylaziridinyl-(1)]-1,3-dihydroxypropane.

EXAMPLE 6

Ethyl α-[2-cyanoaziridinyl-(1)]-α-[2-carbamoylaziridinyl-(1)]-propionate

A solution of 3.4 g. 2-cyanoaziridine in 5 ml. diethyl ether and a solution of 2.9 g. ethyl pyruvate in 5 ml. diethyl ether are carefully mixed together, while cooling to about 10° C. 1.5 ml. triethylamine are then added dropwise, with further cooling to about 20° C. After standing for about 1 to 2 hours at ambient temperature, the reaction mixture is evaporated in a vacuum and the residue is chromatographed on basic aluminum oxide (activity stage III, elution agent successively: heptane, diethyl ether, ethyl acetate). After evaporating the fractions containing the desired substance, there are obtained 3.6 g. ethyl α-[2-cyanoaziridinyl-(1)]-α-[2-carbamoylaziridinyl-(1)]-propionate in the form of a pale yellowish syrup.

In an analogous manner, from 2-cyanoaziridine and ethyl mesoxalate, there is obtained diethyl α-[2-cyanoaziridinyl-(1)]-α-[2-carbamoylaziridinyl-(1)]-malonate.

EXAMPLE 7

2-[2-Cyanoaziridinyl-(1)]-2-[2-carbamoylaziridinyl-(1)]-n-hexane

A mixture of 6.8 g. 2-cyanoaziridine, 10.0 g. hexan-2-one and 2.5 ml. triethylamine are left to stand for 28 days at ambient temperature. The reaction mixture is then evaporated in a vacuum and the residue is chromatographed on basic aluminum oxide (activity stage III, elution agent: heptane/ethyl acetate 9:1 to 6:4). After evaporation of the fractions containing the desired substance, there is obtained a colorless to weakly yellowish syrup which partially crystallizes after standing for a comparatively long period of time. After trituration with diethyl ether, there is obtained 1.5 g. 2-[2-cyanoaziridinyl-(1)]-2-[2-carbamoylaziridinyl-(1)]-n-hexane; m.p. 129°–131° C.

EXAMPLE 8

3-[2-Cyanoaziridinyl-(1)]-3-[2-carbamoylaziridinyl-(1)]pentane

A mixture of 6.8 g. 2-cyanoaziridine, 8.6 g. diethyl ketone and 5 ml. triethylamine is left to stand for 28 days at ambient temperature. The reaction mixture is then evaporated in a vacuum and the residue obtained is chromatographed on basic aluminum oxide (activity stage III, elution agent: initially diethyl ether with an increasing proportion of ethyl acetate, then ethyl acetate). The fractions containing the desired substance are evaporated to give a solid residue which is recrystallized from a little ethyl acetate with the addition of diethyl ether. There are obtained 2.1 g. 3-[2-cyanoaziridinyl-(1)]-3-[2-carbamoylaziridinyl-(1)]-pentane; m.p. 108°–112° C.

In an analogous manner, there are obtained from (a) 2-cyanoaziridine and butan-2-one in the presence of triethylamine:
2-[2-cyanoaziridinyl-(1)]-2-[2-carbamoylaziridinyl-(1)]-butane; colorless to pale yellow syrup;

(b) 2-cyanoaziridine and heptan-2-one in the presence of triethylamine:
4-[2-cyanoaziridinyl-(1)]-4-[2-carbamoylaziridinyl-(1)]-n-heptane; yellowish syrup;

(c) 2-cyanoaziridine and ethyl laevulinate in the presence of triethylamine:
ethyl γ-[2-cyanoaziridinyl-(1)-γ-[2-carbamoylaziridinyl-(1)]-valerate m.p. 146°–150° C.

EXAMPLE 9

1-[2-Cyanoaziridinyl-(1)]-1-[2-carbamoylaziridinyl-(1)]-cyclopropylethane

A mixture of 3.4 g. 2-cyanoaziridine, 4.2 g. cyclopropylmethyl ketone and 2.5 ml. triethylamine is left to stand for 36 days at ambient temperature. The reaction mixture is then evaporated in a vacuum and the residue obtained is chromatographed on basic aluminum oxide (activity stage III, elution agent successively: heptane, diethyl ether and ethyl acetate). The crystalline residue obtained after evaporation of the fractions containing the desired substance is recrystallized from a little ethyl acetate with the addition of diethyl ether. There are obtained 3.1 g. 1-[2-cyanoaziridinyl-(1)]-1-[2-carbamoylaziridinyl-(1)]-1-cyclopropylethane; m.p. 105°–110° C.

In an analogous manner, there are obtained from:

(a) 2-cyanoaziridine and methyl cyclopentyl ketone in the presence of triethylamine:
1-[2-cyanoaziridinyl-(1)]-1-[2-carbamoylaziridinyl-(1)]-1-cyclopentylethane;

(b) 2-cyanoaziridine and ethyl cyclohexyl ketone in the presence of triethylamine:
1-[2-cyanoaziridinyl-(1)]-1-[2-carbamoylaziridinyl-(1)]-1-cyclohexylpropane;

(c) 2-cyanoaziridine and ethyl cyclohexylmethyl ketone in the presence of triethylamine:
2-[2-cyanoaziridinyl-(1)]-2-[2-carbamoylaziridinyl-(1)]-1-cyclohexylbutane;

(d) 2-cyanoaziridine and dicyclohexyl ketone in the presence of triethylamine:
[2-cyanoaziridinyl-(1)]-[2-carbamoylaziridinyl-(1)]-dicyclohexylmethane;

(e) 2-cyanoaziridine and di-cyclohexylmethyl ketone in the presence of triethylamine:
2-[2-cyanoaziridinyl-(1)]-2-[2-carbamoylaziridinyl-(1)]-1,3-dicyclohexylpropane.

EXAMPLE 10

1-[2-Cyanoaziridinyl-(1)]-1-[2-carbamoylaziridinyl-(1)]cyclohexane 50 g. of a mixture of 2-cyanoaziridine and cyclohexanone is kept for about 25-30 days at ambient temperature. The colorless crystals obtained upon scratching with a glass rod or by seeding are triturated with diethyl ether. The crystals are filtered off with suction and recrystallized from methanol. There are obtained 11.0 g. 1-[2-cyanoaziridinyl-(1)]-1-[2-carbamoylaziridinyl-(1)]-cyclohexane; m.p. 191°–193° C.

EXAMPLE 11

1-[2-Cyanoaziridinyl-(1)]-1-[2-carbamoylaziridinyl-(1)]-cyclohexane 5.0 g. of the mixture described in Example 10 are heated to 60° C. for about 40 hours. The light honey-colored crystalline slurry obtained is triturated with diethyl ether and filtered off with suction and the residue is recrystallized from a little methanol. There is obtained 1.1 g. 1-[2-cyanoaziridinyl-(1)]-1-[2-carbamoylaziridinyl-(1)]-cyclohexane; m.p. 190°–192° C.

The mixture of 2-cyanoaziridine and cyclohexanone used in Examples 10 and 11 is obtained in the manner described in German Patent Specification No. 2,309,529 by the reaction of pentamethylene-oxaziridine with acrylonitrile.

EXAMPLE 12

1-[2-Cyanoaziridinyl-(1)]-1-[2-carbamoylaziridinyl-(1)]-cyclohexane

A mixture of 3.4 g. 2-cyanoaziridine and 2.45 g. cyclohexanone is heated to 60° C. for 40 hours. After working up the reaction mixture in a manner analogous to that described in Example 11, there is obtained 0.9 g. (15.5% of theory) 1-[2-cyanoaziridinyl-(1)]-1-[2-carbamoylaziridinyl-(1)]-cyclohexane; m.p. 189°–191° C.

EXAMPLE 13

1-[2-Cyanoaziridinyl-(1)]-1-[2-carbamoylaziridinyl-(1)]-cyclohexane

A solution of 0.68 g. 2-cyanoaziridine, 0.86 g. 2-carbamoylaziridine and 0.98 g. cyclohexanone in 25 ml. acetonitrile is heated to 60° C. for about 100 hours. The reaction mixture is thereafter evaporated and the brownish residue is triturated with diethyl ether and filtered off with suction. After recrystallization from a little methanol, there is obtained 0.28 g. (12% of theory) 1-[2-cyanoaziridinyl-(1)]-1-[2-carbamoylaziridinyl-(1)]-cyclohexane; m.p. 188°–190° C.

EXAMPLE 14

1-[2-Cyanoaziridinyl-(1)]-1-[2-carbamoylaziridinyl-(1)]-cyclohexane.

0.34 g. 2-cyanoaziridine and 0.245 g. cyclohexanone are, after the addition of about 3–4 mg. phenol, initially kept for 5 days at ambient temperature and subsequently heated to 60° C. for 20 hours. The viscous honey-colored residue obtained upon cooling is triturated with diethyl ether and some isopropanol. The yellowish-colored precipitate obtained is filtered off with suction and recrystallized from a little methanol. There is obtained 0.143 g. (24% of theory) 1-[2-cyanoaziridinyl-(1)]-1-[2-carbamoylaziridinyl-(1)]-cyclohexane; m.p. 190°–192° C.

The reaction proceeds in a similar manner when using a catalytic amount of acetyl chloride, pivaloyl chloride or hydrochloric acid.

EXAMPLE 15

1-[2-Cyanoaziridinyl-(1)]-1-[2-carbamoylaziridinyl-(1)]-cyclohexane 68.0 g. 2-cyanoaziridine, 98.0 g. cyclohexanone and 64 ml. triethylamine are carefully mixed, the temperature thereby increasing to about 55° C. The mixture is left to stand for about 6 days at ambient temperature and subsequently the precipitated crystals are filtered off with suction. The crude crystals are dissolved in 700 ml. chloroform-methanol (1:1) and the solution is filtered and then concentrated in a vacuum to a volume of about 200 ml. This concentrate is then left to crystallize overnight and, after filtering off with suction and drying, there are obtained 31.7 g. 1-[2-cyanoaziridinyl-(1)]-1-[2-carbamoylaziridinyl-(1)]-cyclohexane; m.p. 186°–188° C.

EXAMPLE 16

1-[2-Cyanoaziridinyl-(1)]-1-[2-carbamoylaziridinyl-(1)]-cyclohexane

The mother liquor of the pure crystals obtained in Example 15 are evaporated in a vacuum. A part of the syrupy residue (about 25 g.) crystallizes after a few days. The crystals obtained are triturated with ligroin, with the addition of some ethyl acetate, and thereafter filtered off with suction and dried. There are obtained 5.1 g. 1-[2-cyanoaziridinyl-(1)]-1-[2-carbamoylaziridinyl-(1)]-cyclohexane; m.p. 86°–87° C. Upon recrystallizing a sample from cyclohexane, the melting point increases to 88°–89° C.

Since the substance has the same overall composition and structural formula as the compound obtained in the preceding example, it must be a stereoisomeric form thereof.

EXAMPLE 17

1-[2-Cyanoaziridinyl-(1)]-1-[2-carbamoylaziridinyl-(1)]-cyclopentane

To a mixture of 3.4 g. 2-cyanoaziridine and 4.1 g. cyclopentanone kept at ambient temperature, there are added 2 to 4 drops of triethylamine at intervals of about 3–4 days. After about 15 days, the reaction mixture is chromatographed on basic aluminum oxide (activity stage III, elution agent: successively heptane, diethyl ether and ethyl acetate). The syrupy residue obtained upon evaporating the substance-containing fractions, partially crystallizes after some time. After trituration with some diethyl ether/ethyl acetate, there is obtained 0.9 g. 1-[2-cyanoaziridinyl-(1)]-1-[2-carbamoylaziridinyl-(1)]-cyclopentane; m.p. 132°–134° C.

EXAMPLE 18

1-[2-Cyanoaziridinyl-(1)]-1-[2-carbamoylaziridinyl-(1)]-cyclopentane

The mother liquor of the crystals obtained in Example 17 is evaporated in a vacuum and the residue is suspended in diethyl ether. The crystals formed after standing overnight are filtered off with suction. There is obtained 1.7 g. 1-[2-cyanoaziridinyl-(1)]-1-[2-carbamoylaziridinyl-(1)]-cyclopentane; m.p. 92°–94° C. It appears to be a stereoisomeric form of the compound obtained according to Example 17.

EXAMPLE 19

1-[2-Cyanoaziridinyl-(1)]-1-[2-carbamoylaziridinyl-(1)]-4-methylcyclohexane

A mixture of 6.8 g. 2-cyanoaziridine, 5.6 g. 4-methylcyclohexanone and 5 ml. triethylamine is kept at ambient temperature for 6 days. The resultant crystals are separated off after the addition of some diethyl ether and recrystallized twice from about 50 ml. ethyl acetate. There is obtained 1.6 g. 1-[2-cyanoaziridinyl-(1)]-1-[2-carbamoylaziridinyl-(1)]-4-methylcyclohexane; m.p. 150°–151° C.

EXAMPLE 20

1-[2-Cyanoaziridinyl-(1)]-1-[2-carbamoylaziridinyl-(1)]-4-methoxycarbonylcyclohexane 2.5 ml. triethylamine are added, while cooling to ambient temperature, to a mixture of 6.8 g. 2-cyanoaziridine and 7.8 g. 4-methoxycarbonylcyclohexanone. After standing for two days at ambient temperature, the reaction mixture is chromatographed on basic aluminum oxide (activity stage III, elution agent: initially heptane and then heptane/ethyl acetate 95:5 to 80:20). After evaporation of the fractions containing the desired substance, there are obtained 5.6 g. 1-[2-cyanoaziridinyl-(1)]-1-[2-carbamoylaziridinyl-(1)]-4-metoxycarbonylcyclohexane in the form of a pale yellow syrup.

In an analogous manner, there are obtained from 2-cyanoaziridine and (a) 4-hydroxycyclohexanone:
1-[2-cyanoaziridinyl-(1)]-1-[2-carbamoylaziridinyl-(1)]-4-hydroxycyclohexane;

(b) 4-methoxycyclohexanone:
1-[2-cyanoaziridinyl-(1)]-1-[2-carbamoylaziridinyl-(1)]-4-methoxycyclohexane;

(c) 4-ethylenedioxycyclohexanone:
1-[2-cyanoaziridinyl-(1)]-1-[2-carbamoylaziridinyl-(1)]-4-ethylenedioxycyclohexane;

(d) 4-hydroxymethylcyclohexanone:
1-[2-cyanoaziridinyl-(1)]-1-[2-carbamoylaziridinyl-(1)]-4-hydroxymethylcyclohexane;

(e) 2-ethoxycarbonylmethylcyclohexanone:
1-[2-cyanoaziridinyl-(1)]-1-[2-carbamoylaziridinyl-(1)]-2-ethoxycarbonylmethylcyclohexane;

(f) 2-dimethylaminocyclohexanone:
1-[2-cyanoaziridinyl-(1)]-1-[2-carbamoylaziridinyl-(1)]-2-dimethylaminocyclohexane;

(g) cycloheptanone:
1-[2-cyanoaziridinyl-(1)]-1-[2-carbamoylaziridinyl-(1)]-cycloheptane;

(h) cyclooctanone:
1-[2-cyanoaziridinyl-(1)]-1-[2-carbamoylaziridinyl-(1)]-cyclooctane;

(i) adamantan-2-one:
2-[2-cyanoaziridinyl-(1)]-2-[2-carbamoylaziridinyl-(1)]-adamantane.

EXAMPLE 21

1,3-Bis-[2-cyanoaziridinyl-(1)]-1-[2-carbamoylaziridinyl-(1)]-cyclohexane

A mixture of 4.8 g. 2-cyclohexen-1-one, 3.4 g. 2-cyanoaziridine and 3.5 ml. triethylamine is stirred for 4 days at ambient temperature. The initially clear solution thereby becomes turbid. The upper triethylamine phase is separated off and the remaining oil is first stirred several times with diethyl ether, which is poured off. The oil is thereafter stirred with butyl acetate and the butyl acetate extract is mixed with diethyl ether, 1.25 g. of beige-colored crystals thereby being obtained which do not possess a sharp melting point. Further purification is carried out by column chromatography with basic aluminum oxide (activity stage III, elution agent: chloroform-methanol 9:1). There is thus obtained 0.56 g. of white 1,3-bis-[2-cyanoaziridinyl-(1)]-1-[2-carbamoylaziridinyl-(1)]-cyclohexane; m.p. 74°–81° C. (bubble formation).

In an analogous manner, from 2-cyanoaziridine and 2-benzoylthiophene, there is obtained [2-cyanoaziridinyl-(1)]-[2-carbamoylaziridinyl-(1)]-phenyl-[thienyl-(2)]-methane; m.p. 159°–164° C.

EXAMPLE 22

Methyl α-[2-cyanoaziridinyl-(1)]-α-[2-carbamoylaziridinyl-(1)]-phenylacetate

A mixture of 8.2 g. methylphenylglyoxylate, 3.4 g. 2-cyanoaziridine and 3.5 ml. triethylamine is stirred in a bath for 10 minutes at 100° C. After cooling, the reaction mixture is stirred several times with diethyl ether, which is poured off, and the ether-insoluble residue is taken up in chloroform, filtered with charcoal and the filtrate mixed with ligroin. The product which separates out becomes crystalline upon the addition of diethyl ether. There is thus obtained 4.9 g. methyl α-[2-cyanoaziridinyl-(1)]-α-[2-carbamoylaziridinyl-(1)]-phenylacetate. Further purification is carried out by dissolving in ethyl acetate and precipitating with diethyl ether. The product then melts at 74° C. and foams at 80° C.

In an analogous manner, there are obtained from 2-cyanoaziridine and (a) phenylacetone:
2-[2-cyanoaziridinyl-(1)]-2-[2-carbamoylaziridinyl-(1)]-1-phenylpropane; m.p. 112°–118° C.

(b) p-methoxyacetophenone:
1-[2-cyanoaziridinyl-(1)]-1-[2-carbamoylaziridinyl-(1)]-1-p-methoxyphenylethane;

(c) p-(methoxycarbonyl)-acetophenone in the presence of potassium carbonate:
1-[2-cyanoaziridinyl-(1)]-1-[2-carbamoylaziridinyl-(1)]-1-(p-methoxycarbonylphenyl)-ethane;

(d) 2-benzoylfuran:
[2-cyanoaziridinyl-(1)]-[2-carbamoylaziridinyl-(1)]-phenyl-[furyl-(2)]-methane; m.p. 58°–62° C.

EXAMPLE 23

1-[2-Cyanoaziridinyl-(1)]-1-[2-carbamoylaziridinyl-(1)]-1-phenylethane

A suspension of 0.3 g. potassium carbonate in 2.4 g. acetophenone and 2.7 g. 2-cyanoaziridine is stirred at ambient temperature. After 3 days, the reaction mixture is extracted several times with diethyl ether and the insoluble residue is taken up in ethyl acetate, filtered and mixed with ligroin, no crystallisation thereby taking place, whereafter the solvent is removed in a high vacuum. There is thus obtained 1.5 g. of oily 1-[2-cyanoaziridinyl-(1)]-1-[2-carbamoylaziridinyl-(1)]-1-phenylethane.

EXAMPLE 24

1-[2-Cyanoaziridinyl-(1)]-1-[2-carbamoylaziridinyl-(1)]-1-phenylpropane

A suspension of 2 g. basic aluminum oxide in 5.4 g. propiophenone and 2.7 g. 2-cyanoaziridine is stirred at ambient temperature. After one week, the reaction mixture is diluted with methanol, filtered and the filtrate evaporated. After repeated treatment with diethyl ether-ligroin, the residue is freed from solvent in a high vacuum to give 0.95 g. of oily 1-[2-cyanoaziridinyl-(1)]-1-[2-carbamoylaziridinyl-(1)]-1-phenylpropane.

In an analogous manner, there is obtained from 2-cyanoaziridine and (a) phenoxyacetone:

2-[2-cyanoaziridinyl-(1)]-2-[2-carbamoylaziridinyl-(1)]-1-phenoxypropane; decomposes slowly at 50° C.
(b) p-chloroacetophenone:
1-[2-cyanoaziridinyl-(1)]-1-[2-carbamoylaziridinyl-(1)]-(p-chlorophenyl)-ethane; oily product;
(c) p-methylacetophenone:
1-[2-cyanoaziridinyl-(1)]-1-[2-carbamoylaziridinyl-(1)]-1-p-tolylethane; oily product;
(d) cyclopropyl phenyl ketone:
[2-cyanoaziridinyl-(1)]-[2-carbamoylaziridinyl-(1)]-cyclopropylphenylmethane.

EXAMPLE 25

9-[2-cyanoaziridinyl-(1)]-9-[2-carbamoylaziridinyl-(1)]-fluorene

A suspension of 1.8 g. fluoren-9-one in 2 ml. 2-cyanoaziridine and 0.7 ml. triethylamine is stirred for 1 hour at 50° C., solution thereby taking place. After 2 days at ambient temperature, the reaction mixture is stirred several times with diethyl ether, the remaining grease is taken up in chloroform and the extract is washed with water, dried and evaporated. The residue becomes crystalline when diethyl ether is added thereto. There is thus obtained 0.4 g. 9-[2-cyanoaziridinyl-(1)]-9-[2-carbamoylaziridinyl-(1)]-fluorene; m.p. 140° C.

EXAMPLE 26

α-[2-Cyanoaziridinyl-(1)]-α-[2-carbamoylaziridinyl-(1)]-diphenylmethane

In a manner analogous to that described in Example 25, benzophenone is reacted with 2-cyanoaziridine in the presence of triethylamine. After column chromatographic purification of the reaction mixture, there is obtained a high melting fraction (m.p. 171°–174° C.) and a low melting fraction (above 78° C. bubble formation) of α-[2-cyanoaziridinyl-(1)]-α-[2-carbamoylaziridinyl-(1)]-diphenylmethane.

EXAMPLE 27

1-[2-Cyanoaziridinyl-(1)]-1-[2-carbamoylaziridinyl-(1)]-ethane 2.6 g. acetaldehyde are added to a solution of 8.2 g. 2-cyanoaziridine and 2.8 ml. triethylamine in 15 ml. ethyl acetate and the resultant reaction mixture is subsequently stirred for 24 hours at ambient temperature. The course of the reaction is monitored by thin layer chromatography (Merck DC-finished plate silica gel 60F 254; elution agent: acetonitrile/chloroform/cyclohexane 5:5:1; spray reagent 0.5% solution of p-dimethylaminobenzaldehyde in n-butanol/ethanol/concentrated hydrochloric acid 6:1:0.1). The crystalline slurry which separates out is separated off by filtration, washed with some ethyl acetate or diethyl ether and then recrystallized from ethanol. There are obtained 3.4 g. 1-[2-cyanoaziridinyl-(1)]-1-[2-carbamoylaziridinyl-(1)]-ethane; m.p. 170°–172° C.

In an analogous manner, there is obtained from 2-cyanoaziridine and
(a) isobutyraldehyde:
1-[2-cyanoaziridinyl-(1)]-1-[2-carbamoylaziridinyl-(1)]-2-methylpropane; m.p. 196°–197° C.
(b) formaldehyde:
1-[2-cyanoaziridinyl-(1)]-1-[2-carbamoylaziridinyl-(1)]-methane; m.p. 132°–135° C.;
(c) trimethylacetaldehyde:
1-[2-cyanoaziridinyl-(1)]-1-[2-carbamoylaziridinyl-(1)]-2,2-dimethylpropane; m.p. 164°–166° C.
(d) propionaldehyde:
1-[2-cyanoaziridinyl-(1)]-1-[2-carbamoylaziridinyl-(1)]-propane; m.p. 168°–169° C.;
(e) butyraldehyde:
1-[2-cyanoaziridinyl-(1)]-1-[2-carbamoylaziridinyl-(1)]-butane; m.p. 167°–169° C.;
(f) 2-ethylbutyraldehyde:
1-[2-cyanoaziridinyl-(1)]-1-[2-carbamoylaziridinyl-(1)]-2-ethylbutane;
(g) methoxyacetaldehyde:
1-[2-cyanoaziridinyl-(1)]-1-[2-carbamoylaziridinyl-(1)]-2-metoxyethane; m.p. 192°–193° C.;
(h) 3-methoxypropionaldehyde:
1-[2-cyanoaziridinyl-(1)]-1-[2-carbamoylaziridinyl-(1)]-3-methoxypropane; m.p. 148°–150° C.

EXAMPLE 28

3-[2-Cyanoaziridinyl-(1)]-3-[2-carbamoylaziridinyl-(1)]-tetrahydrothiapyran 5.8 g. tetrahydrothiapyr-3-one are added to a solution of 6.8 g. 2-cyanoaziridine and 1.7 ml. triethylamine in 12 ml. ethyl acetate and the resultant reaction mixture is stirred for 24 hours at ambient temperature. The course of the reaction is monitored by thin layer chromatography (cf. Example 27). The crystalline slurry which separates out is then filtered off with suction and thoroughly washed several times with ethyl acetate and dried. There are obtained 4.3 g. 3-[2-cyanoaziridinyl-(1)]-3-[2-carbamoylaziridinyl-(1)]-tetrahydrothiapyran; m.p. 178°–180° C.

In an analogous manner, there is obtained from 2-cyanoaziridine and
(a) tetrahydropyran-4-one:
4-[2-cyanoaziridinyl-(1)]-4-[2-carbamoylaziridinyl-(1)]-tetrahydropyran; m.p. 162°–165° C.;
(b) cyclohexanecarboxaldehyde:
[2-cyanoaziridinyl-(1)]-[2-carbamoylaziridinyl-(1)]-cyclohexylmethane; m.p. 214°–215° C.;
(c) indan-2-one:
2-[2-cyanoaziridinyl-(1)]-2-[2-carbamoylaziridinyl-(1)]-indane;
(d) tetral-1-one:
1-[2-cyanoaziridinyl-(1)]-1-[2-carbamoylaziridinyl-(1)]-1,2,3,4-tetrahydronaphthalene;
(e) cyclohexan-1,4-dione:
1-[2-cyanoaziridinyl-(1)]-1-[2-carbamoylaziridinyl-(1)]-cyclohexan-4-one; m.p. 108°–109° C.;
(f) tetrahydrothiapyr-4-one-1-oxide:
4-[2-cyanoaziridinyl-(1)]-4-[2-carbamoylaziridinyl-(1)]-tetrahydrothiapyran-1-oxide;
(g) tetrahydrothiapyr-4-one-1,1-dioxide:
4-[2-cyanoaziridinyl-(1)]-4-[2-carbamoylaziridinyl-(1)]-tetrahydrothiapyran-1,1-dioxide;
(h) N-methylpiperid-3-one:
3-[2-cyanoaziridinyl-(1)]-3-[2-carbamoylaziridinyl-(1)]-1-methylpiperidine;
(i) N-acetyl-piperid-3-one:
3-[2-cyanoaziridinyl-(1)]-3-[2-carbamoylaziridinyl-(1)]-1-acetyl-piperidine;
(k) 3-oxa-9-aza-9-methyl-bicyclo[3.3.1]nonane:
3-[2-cyanoaziridinyl-(1)]-3-[2-carbamoylaziridinyl-(1)]-9-aza-9-methyl-bicyclo[3.3.1]nonane;
(l) cyclohexyl-thienyl-(2) ketone:
[2-cyanoaziridinyl-(1)]-[2-carbamoylaziridinyl-(1)]-cyclohexyl-[thienyl-(2)]-methane.

EXAMPLE 29

[2-Cyanoaziridinyl-(1)]-[2-carbamoylaziridinyl-(1)]-phenylmethane

A mixture of 3.4 g. 2-cyanoaziridine, 2.6 g. benzaldehyde and 1 ml. triethylamine is maintained at 60° C. for 10 hours. After cooling, the reaction mixture solidifies to a solid crystalline mass which is washed out with ethyl acetate or diethyl ether. The solid material is then filtered off and dried. After recrystallization from ethyl acetate, there are obtained 2.2 g. [2-cyanoaziridinyl-(1)]-[2-carbamoylaziridinyl-(1)]-phenylmethane; m.p. 158°–160° C.

In an analogous manner, there is obtained from 2-cyanoaziridine and (a) cyclohexane-carboxaldehyde:
[2-cyanoaziridinyl-(1)]-[2-carbamoylaziridinyl-(1)]-cyclohexylmethane; m.p. 213°–216° C.;

(b) 4-chlorobenzaldehyde:
[2-cyanoaziridinyl-(1)]-[2-carbamoylaziridinyl-(1)]-(4-chlorophenyl)-methane; m.p. 189°–192° C.;

(c) 4-dimethylaminobenzaldehyde:
[2-cyanoaziridinyl-(1)]-[2-carbamoylaziridinyl-(1)]-(dimethylaminophenyl)-methane; m.p. 204°–206° C.;

(d) furfural:
[2-cyanoaziridinyl-(1)]-[2-carbamoylaziridinyl-(1)]-[furyl-(2)]-methane; m.p. 171°–173° C.;

(e) thiophene-(2)-aldehyde:
[2-cyanoaziridinyl-(1)]-[2-carbamoylaziridinyl-(1)]-[thienyl-(2)]-methane; m.p. 182°–185° C.;

(f) 3-nitrobenzaldehyde:
[2-cyanoaziridinyl-(1)]-[2-carbamoylaziridinyl-(1)]-(3-nitrophenyl)-methane; m.p. 180°–183° C.

EXAMPLE 30

[2-Cyanoaziridinyl-(1)]-[2-carbamoylaziridinyl-(1)]-(3-nitrophenyl)-methane 11.3 g. 3-nitrobenzaldehyde are added to a solution of 10.2 g. 2-cyanoaziridine and 3 ml. triethylamine in 30 ml. ethyl acetate, whereafter the reaction mixture is stirred for 80 hours at ambient temperature. The crystalline precipitate is then filtered off with suction, washed with ether and recrystallized from ethyl acetate. There are obtained 6.7 g. [2-cyanoaziridinyl-(1)]-[2-carbamoylaziridinyl-(1)]-(3-nitrophenyl)-methane; m.p. 181°–183° C.

In an analogous manner, there is obtained from 2-cyanoaziridine and (a) o-tolylaldehyde:
[2-cyanoaziridinyl-(1)]-[2-carbamoylaziridinyl-(1)]-(2-methylphenyl)-methane; m.p. 158°–161° C.;

(b) 3-methoxybenzaldehyde:
[2-cyanoaziridinyl-(1)]-[2-carbamoylaziridinyl-(1)]-(3-methoxyphenyl)-methane; m.p. 161°–163° C.;

(c) 4-hydroxybenzaldehyde:
[2-cyanoaziridinyl-(1)]-[2-carbamoylaziridinyl-(1)]-(4-hydroxyphenyl)-methane; m.p. 161°–163° C.;

(d) p-methoxycarbonyl-benzaldehyde:
[2-cyanoaziridinyl-(1)]-[2-carbamoylaziridinyl-(1)]-(4-methoxycarbonylphenyl)-methane; m.p. 182°–185° C.;

(e) 2,5-dimethylbenzaldehyde:
[2-cyanoaziridinyl-(1)]-[2-carbamoylaziridinyl-(1)]-(2,5-dimethylphenyl)-methane; m.p. 165°–168° C.;

(f) piperonal:
[2-cyanoaziridinyl-(1)]-[2-carbamoylaziridinyl-(1)]-(3,4-methylenedioxyphenyl)-methane; m.p. 207°–209° C.;

(g) 2,4-dichlorobenzaldehyde:
[2-cyanoaziridinyl-(1)]-[2-carbamoylaziridinyl-(1)]-(2,4-dichlorophenyl)-methane;

(h) 4-cyanobenzaldehyde:
[2-cyanoaziridinyl-(1)]-[2-carbamoylaziridinyl-(1)]-(4-cyanophenyl)-methane;

(i) 4-methylthiobenzaldehyde:
[2-cyanoaziridinyl-(1)]-[2-carbamoylaziridinyl-(1)]-(4-methylthiophenyl)-methane;

(k) 3-trifluoromethylbenzaldehyde:
[2-cyanoaziridinyl-(1)]-[2-carbamoylaziridinyl-(1)]-(3-trifluoromethylphenyl)-methane;

(l) 4-carbamoylbenzaldehyde:
[2-cyanoaziridinyl-(1)-[2-carbamoylaziridinyl-(1)]-(4-carbamoylphenyl)-methane;

(m) 4-sulphamoylbenzaldehyde:
[2-cyanoaziridinyl-(1)]-[2-carbamoylaziridinyl-(1)]-(4-sulphamoylphenyl)-methane.

EXAMPLE 31

3-[2-Cyanoaziridinyl-(1)]-3-[2-carbamoylaziridinyl-(1)]-1-phenylprop-1-one 6.6 g. cinnamaldehyde and 6.8 g. 2-cyanoaziridine are, after the addition of 2.5 ml. triethylamine, kept at ambient temperature for 72 hours. The reaction mixture, which solidifies to a crystalline mass, is slurried with ethyl acetate and the solid material is filtered off with suction and recrystallized from ethanol. There are obtained 4.6 g. 3-[2-cyanoaziridinyl-(1)]-3-[2-carbamoylaziridinyl-(1)]-1-phenylprop-1-ene; m.p. 166°–168° C.

In an analogous manner, there is obtained from 2-cyanoaziridine and (a) N-methylpyrrol-2-aldehyde:
2-{[2-cyanoaziridinyl-(1)]-[2-carbamoylaziridinyl-(1)]-methyl}-1-methylpyrrole;

(b) furfural:
[2-cyanoaziridinyl-(1)]-[2-carbamoylaziridinyl-(1)]-[furyl-(2)]-methane; m.p. 171°–173° C.;

(c) thiophene-2-aldehyde:
[2-cyanoaziridinyl-(1)]-[2-carbamoylaziridinyl-(1)]-[thienyl-(2)]-methane; m.p. 182°–185° C.;

(d) 4-cyclohex-1-ene-aldehyde:
[2-cyanoaziridinyl-(1)]-[2-carbamoylaziridinyl-(1)]-(cyclohex-3-enyl)-methane; m.p. 195°–198° C.;

(e) 5,6-dihydro-2H-3-formyl-pyran:
[2-cyanoaziridinyl-(1)]-[2-carbamoylaziridinyl-(1)]-[5,6-dihydro-2H-pyranyl-(3)]-methane; m.p. 190°–192° C.;

(f) 2-oxo-bicyclo[2.2.1]heptane:
2-[2-cyanoaziridinyl-(1)]-2-[2-carbamoylaziridinyl-(1)]-bicyclo[2.2.1]heptane; m.p. 148°–151° C.

EXAMPLE 32

1,1-Bis-[2-cyanoaziridinyl-(10)]-cyclohexane

To a mixture of 10 g. 2-cyanoaziridine and 20 g. cyclohexanone, there is initially added 0.5 ml. ethereal hydrogen chloride solution and this addition is repeated at intervals of about 8–10 days. After standing for a total of 30 days at ambient temperature, the reaction mixture is added dropwise to about 500 ml. diethyl ether and the precipitate formed is filtered off with suction. The mother liquor is evaporated and chromatographed on basic aluminum oxide (activity stage III, elution agent: diethyl ether and then ethyl acetate). After evaporation of the fraction containing the desired material, there is obtained 1,1-bis-[2-cyanoaziridinyl-(1)]-cyclohexane; m.p. 105°–106° C.

EXAMPLE 33

1,1-Bis-[2-cyanoaziridinyl-(1)]-cyclohexane 3.3 g. Triphenyl phosphine and 2.3 g. 1-[2-cyanoaziridinyl-(1)]-1-[2-carbamoylaziridinyl-(1)]-cyclohexane (cf. Examples 10–15) are added to a mixture of 10 ml. chloroform, 1.5 g. carbon tetrachloride and 1.0 g. triethylamine. The suspension is heated, while stirring, to about 50° C. After 6 hours, the reaction mixture is evaporated and the residue is taken up in diethyl ether. Insoluble material is filtered off with suction and the filtrate is chromatographed on a column of silica gel, using diethyl ether as elution agent. After evaporation of the fractions containing the desired substance and trituration of the residue with a little diethyl ether, there is obtained 0.6 g. 1,1-bis-[2-cyanoaziridinyl-(1)]-cyclohexane; m.p. 105°–106° C.

EXAMPLE 34

In an analogous manner there is obtained from methyl-α-[2-cyanoaziridinyl-(1)]-α-[2-carbamoylaziridinyl-(1)]-phenylacetate (see Example 22) a rough product, which is divided by being chromatographed on silica gel with heptane/ethyl acetate 2:1 as eluting agent into two isomers of methyl-α,α-bis-[2-cyanoaziridinyl-(1)]-phenylacetate with melting points of 139°–142° C. and 83°–86° C.

The pharmacological properties of the new compound were determined as follows:

PHARMACOLOGICAL TESTS

1. Cancerostatic Effect

Ready-to-be-transplanted tumors of various kinds were taken from freshly killed rats, comminuted coarsely and pulverized with addition of 8 ml of physiological sodium chloride solution. Female Sprague-Dawley rats weighing 80 to 100 g were used as test animals. The respective tumor cell suspension was applied subfacially to the animals in an amount of 0.5 ml per animal under sterile conditions in the neck area. On the seventh day after the transplantation the animals were killed, the tumors taken out and weighed. The substances according to the instant invention were in each case applied orally three days prior to the tumor application by means of a throat tube (in 10 ml 1% hydrous methylhydroxylethyl cellulose solution per kg of body weight). The following tables contain averages of the respective test groups of 20 animals and show that the tumor growth was significantly inhibited.

(a) Walker-Carcinoma 256

TABLE 1

| Active Material | Dose, mg/kg | Tumor weight, g | Difference % |
|---|---|---|---|
| Example 10 | 10.0 | 7.9 | −6.0 |
|  | 50.0 | 5.0 | −41.7 |
|  | 100.0 | 4.5 | −46.9 |
| Control | — | 8.5 | — |
| Example 1 | 5.0 | 11.8 | −27.1 |
|  | 50.0 | 12.1 | −25.4 |
|  | 100.0 | 15.6 | −4.1 |
| Control | — | 16.2 | — |

(b) DC-Carcino-Sarcoma

TABLE 2

| Active Material | Dose, mg/kg | Tumor weight, g | Difference % |
|---|---|---|---|
| Example 10 | 100 | 10.9 | −40.0 |
|  | 50 | 11.0 | −38.5 |
| Example 1 | 300 | 9.8 | −45.0 |
|  | 150 | 5.9 | −67.0 |
| Control | — | 17.9 | — |

IMMUNITY-STIMULATING ACTIVITY (a) Alteration of the leucocyte number

The active substance was dissolved in each case in 10 ml of a 1% methyl-hydroxyethyl cellulose solution per kg of body weight and orally applied by means of a neck tube to ten fasting female Sprague-Dawley rats in each case. On the fourth day, blood was taken retroorbitally and the leucocyte number was determined by means of a coult counter. The following table containing the proportions of the averages of the leucocyte numbers of the test group to those of the control group shows that, with an application of 50–200 mg per kg of body weight, all substances significantly increased the leucocyte number and thereby the immunity defense of the test animal.

TABLE 3

| Compound of Example | 200 mg | 50 mg |
|---|---|---|
| 1 | 1,55 | 1,70 |
| 3 | 1,82 | 1,42 |
| 6 | 1,65 | 1,15 |
| 8 b | 1,38 | 1,26 |
| 9 | 1,82 | 1,32 |
| 10 | 2,06 | 0,92 |
| 16 | 1,50 | 1,30 |
| 19 | 1,36 | 1,00 |
| 20 | 1,51 | 1,23 |
| 21 | 1,30 | 1,11 |
| 26 | 1,20 | 1,25 |
| 26 a | 1,30 | 1,00 |
| 27 | 1,53 | 1,17 |
| 27 a | 1,66 | 1,19 |
| 27 d | 1,78 | 1,40 |
| 27 e | 1,36 | 1,30 |
| 28 | 1,80 | 1,26 |
| 28 a | 1,30 | 1,09 |
| 28 b | 1,55 | 1,20 |
| 29 b | 1,40 | 1,00 |
| 29 d | 1,30 | 1,00 |
| 29 e | 1,50 | 1,15 |
| 29 f | 1,26 | 1,09 |
| 30 a | 1,34 | 1,40 |
| 30 b | 1,31 | 1,22 |
| 30 c | 2,21 | 1,70 |
| 30 d | 1,50 | 1,08 |
| 31 | 1,41 | 1,13 |
| 32 | 1,50 | 1,50 |

(b) Resistance increase in case of *Candida albicans* Infection

Female, adult NMRI mice weighing 25–30 g were infected with *Candida albicans*-219. A suspension of approximately 300,000 germs in 0.2 ml physiological sodium chloride per animal was given intravenously. One hour later, 50 mg of the compound of Example 1, per kg body weight, were applied orally by way of neck tube, dissolved in 10 ml 0.1% methyl-hydroxyethyl cellulose. The control group received the same solution without active material. After six days, 18 of the 30 animals of the control group were dead, but only 3 of the 30 animals of the test group, which corresponds to a survival rate of 90% and makes clearly evident the resistance-increasing effect. In vitro tests showed that the active material had no fungistatic effect vis-a-vis *Candida albicans.*

3. Toxicity

The acute toxicity (LD$_{50}$) of the compound of Example 1 in a single intraperitonal administration, amounts to 2550 mg/kg in rats and 2270 mg/kg in mice. The LD$_{50}$ upon oral administration to rats was 3100 mg/kg. These values are much higher than the pharmacologically effective dosages (0.5–50 mg/kg body weight).

From the above experiments, it can be deduced that for the desired pharmacological effect of immunity stimulation, a dosage of about 1 to 50 mg/kg body weight is necessary, which can be administered either all at once or in several individual doses. Since the effect slowly decreases after about 2 weeks, a further treatment can possibly be necessary.

The present invention also provides pharmaceutical compositions comprising the new compound and/or at least one physiologically compatible salt thereof, in admixture with a solid or liquid pharmaceutical diluent or carrier.

For the preparation of pharmaceutical compositions, a 2-cyano-aziridinyl-(1)-2-substituted-aziridinyl-(1)-methane is mixed in known manner with an appropriate pharmaceutical carrier substance and formed, for example, into tablets or dragees or, with the addition of appropriate adjuvants, suspended or dissolved in water or an oil, for example olive oil, and placed in capsules. Since the active material is acid labile, the composition is provided with a coating which only dissolves in the alkaline medium of the intestines or an appropriate carrier material, for example a high molecular weight fatty acid or carboxymethyl-cellulose is mixed therewith. Examples of solid carrier materials include starch, lactose, mannitol, methyl cellulose, talc, highly dispersed silicic acids, high molecular weight fatty acids (for example stearic acid), gelatin, agar-agar, calcium phosphate, magnesium stearate, animal and vegetable fats and solid high molecular weight polymers (such as polyethylene glycols). Compositions suitable for oral administration can, if desired, contain flavoring and/or sweetening materials.

However, the active material is preferably injected. As injection medium, it is preferred to use water which contains the additives usual in the case of injection solutions, such as stabilizing agents, solubilizing agents and/or weakly alkaline buffers. Additives of this type include, for example, phosphate and carbonate buffers, ethanol, complex-forming agents (for example ethylenediamine-tetraacetic acid and the non-toxic salts thereof) and high molecular weight polymers (for example liquid polyethylene oxide) for viscosity regulation.

For treatment of humans the active material may be applied one or more times with each dose containing about 25 to 3000 and preferably about 50 to 500 mg of active material.

It will be appreciated that the instant specification and examples are set forth by way of illustration and not limitation, and that various modifications and changes may be made without departing from the spirit and scope of the present invention.

What is claimed is:

1. A 2-cyanoaziridinyl-(1)-2-substituted-aziridinyl-(1)-methane of the formula

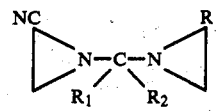

wherein

R is a nitrile or carbamoyl group, and

R$_1$ and R$_2$, which can be the same or different, are hydrogen atoms, alkoxycarbonyl, the alkoxy moiety having up to 6 carbon atoms, or aliphatic hydrocarbon radicals containing up to 10 carbon atoms, which can be straightchained, branched or cyclic, or R$_1$ and R$_2$ together with the carbon atom to which they are attached form a carbocyclic ring containing up to 8 ring members.

2. A 2-cyanoaziridinyl-(1)-2-substituted-aziridinyl-(1)-methane according to claim 1 wherein R is a carbamoyl group, and R$_1$ and R$_2$, which can be the same or different, are hydrogen atoms, alkoxycarbonyl, the alkoxy moiety having up to 3 carbon atoms, or aliphatic hydrocarbon radicals containing up to 6 carbon atoms, which can be straightchained, branched or cyclic.

3. A 2-cyanoaziridinyl-(1)-2-substituted-aziridinyl-(1)-methane according to claim 1 wherein R is a carbamoyl group, and R$_1$ and R$_2$, which can be the same or different, are hydrogen atoms, alkoxycarbonyl, the alkoxy moiety having up to 3 carbon atoms, cyclopropyl or aliphatic hydrocarbon radicals containing up to 6 carbon atoms, which can be straightchained or branched.

4. A compound according to claim 1 wherein such compound is 1,1-bis-[2-cyanoaziridinyl-(1)]-cyclohexane.

5. A method for stimulating the immune response of an animal patient which comprises administering to said patient an effective amount of one of the following compounds 2-(2-cyanoaziridinyl-(1))-2-(2-carbamoylaziridinyl-(1))-propane, 1-(2-cyanoaziridinyl-(1))-1-(2-carbamoylaziridinyl-(1))-1-cyclopropyl-ethane, ethyl α-(2-cyanoaziridinyl-(1))-α-(2-carbamoylaziridinyl(1))-propionate, diethyl 1-(2-cyanoaziridinyl-(1))-1-(2-carbamoylaziridinyl-(1))-2-methyl-propane, 2-(2-cyanoaziridinyl-(1))-2-(2-carbamoylaziridinyl(1))-n-hexane, 1-(2-cyanoaziridinyl-(1))-1-(2-carbamoylaziridinyl(1))-propane, 4-(2-cyanoaziridinyl-(1))-4-(2-carbamoylaziridinyl-(1))-n-heptane, and 1,1-bis-(2-cyanoaziridinyl-(1))-cyclohexane.

6. A compound according to claim 1 wherein such compound is 4-[2-cyanoaziridinyl-(1)]-4-[2-carbamoylaziridinyl-(1)]-n-heptane.

7. A compound according to claim 1 wherein such compound is 2-[2-cyanoaziridinyl-(1)]-2-[2-carbamoylaziridinyl-(1)]propane.

8. A compound according to claim 1 wherein such compound is 1-[2-cyanoaziridinyl-(1)]-1-[2-carbamoylaziridinyl-(1)]-1-cyclopropyl-ethane.

9. A compound according to claim 1 wherein such compound is ethyl α-[2-cyanoaziridinyl-(1)]-α-[2-carbamoylaziridinyl-(1)]-propionate.

10. A compound according to claim 1 wherein such compound is diethyl 1-[2-cyanoaziridinyl-(1)]-1-[2-carbamoylaziridinyl-(1)]-2-methyl-propane.

11. A compound according to claim 1 wherein such compound is 2-[2-cyanoaziridinyl-(1)]-2-[2-carbamoylaziridinyl-(1)]-n-hexane.

12. A compound according to claim 1 wherein such compound is 1-[2-cyanoaziridinyl-(1)]-1-[2-carbamoylaziridinyl-(1)]-propane.

* * * * *

UNITED STATES PATENT AND TRADEMARK OFFICE
CERTIFICATE OF CORRECTION

PATENT NO. : 4,370,323

DATED : Jan. 25, 1983

INVENTOR(S) : Wolfgang Kampe et al.

It is certified that error appears in the above-identified patent and that said Letters Patent is hereby corrected as shown below:

On the title page, Insert Foreign Priority Data

-- July 20, 1976   Fed. Rep. of Germany    26 32517
   Dec. 11, 1976   Fed. Rep. of Germany    26 56240 --.

Signed and Sealed this

Sixteenth Day of August 1983

[SEAL]

*Attest:*

GERALD J. MOSSINGHOFF

*Attesting Officer*   *Commissioner of Patents and Trademarks*